US008649584B2

(12) United States Patent
Kawasaki

(10) Patent No.: US 8,649,584 B2
(45) Date of Patent: Feb. 11, 2014

(54) MEDICAL IMAGE PROCESSING APPARATUS AND MEDICAL IMAGE PROCESSING METHOD

(75) Inventor: Tomohiro Kawasaki, Otawara (JP)

(73) Assignees: Kabushiki Kaisha Toshiba, Tokyo (JP); Toshiba Medical Systems Corporation, Tochigi-Ken (JP)

( * ) Notice: Subject to any disclaimer, the term of this patent is extended or adjusted under 35 U.S.C. 154(b) by 64 days.

(21) Appl. No.: 13/227,796

(22) Filed: Sep. 8, 2011

(65) Prior Publication Data

US 2012/0063663 A1 Mar. 15, 2012

(30) Foreign Application Priority Data

Sep. 15, 2010 (JP) .................. 2010-207207

(51) Int. Cl.
*G06K 9/00* (2006.01)
(52) U.S. Cl.
USPC ........... 382/131; 382/128; 382/130; 382/132; 382/133
(58) Field of Classification Search
USPC ........................................ 382/128, 130–132
See application file for complete search history.

(56) References Cited

U.S. PATENT DOCUMENTS

| 7,920,734 | B2* | 4/2011 | Rinck et al. | 382/131 |
|---|---|---|---|---|
| 7,970,193 | B2* | 6/2011 | Rouet et al. | 382/131 |
| 8,019,142 | B2* | 9/2011 | Nowinski et al. | 382/131 |
| 8,126,238 | B2* | 2/2012 | Skinner et al. | 382/131 |
| 8,199,984 | B2* | 6/2012 | Mori et al. | 382/128 |
| 8,355,775 | B2* | 1/2013 | Oshiki et al. | 600/425 |
| 2004/0249270 | A1 | 12/2004 | Kondo et al. | |
| 2006/0142983 | A1 | 6/2006 | Sorensen et al. | |
| 2009/0010519 | A1* | 1/2009 | Wakai et al. | 382/131 |
| 2010/0040200 | A1* | 2/2010 | Ema et al. | 378/98.12 |

FOREIGN PATENT DOCUMENTS

| EP | 2 157 546 A2 | 2/2010 |
|---|---|---|
| JP | 2003-164452 A | 6/2003 |
| JP | 2009-028515 A | 2/2009 |
| JP | 2009-106530 A | 5/2009 |
| JP | 2010-131315 A | 6/2010 |

OTHER PUBLICATIONS

Extended European Search Report dated Mar. 19, 2012 for corresponding EP Application No. 11180600.6.
Le, Huy, Wong, Jerry T., and Molloi, Sabee, Estimation of regional myocardial mass at risk based on distal arterial lumen volume and length using 3D micro-CT images, Computerized Medical Imaging and Graphics, Pergamon Press, New York, NY, US, vol. 32, No. 6, Sep. 1, 2008, pp. 488-501.

* cited by examiner

*Primary Examiner* — Utpal Shah
(74) *Attorney, Agent, or Firm* — Yoshida & Associates, LLC

(57) ABSTRACT

A medical image processing apparatus includes a vessel running data generating unit, a lesion site detecting unit, a vessel dominant region data generating unit, a lesion site dominant region data generating unit, and a diagnostic image data generating unit. The vessel running data generating unit generates vessel running data of a vessel. The lesion site detecting unit detects positional information of a lesion site in the vessel. The vessel dominant region data generating unit generates vessel dominant region data indicating a region dominated by the vessel in a region provided with nutrition. The lesion site dominant region data generating unit generates lesion site dominant region data indicating a region dominated by the lesion site in the region provided with nutrition. The diagnostic image data generating unit generates diagnostic image data by superimposing the vessel dominant region data and the lesion site dominant region data on morphological image data.

20 Claims, 14 Drawing Sheets

US 8,649,584 B2

MEDICAL IMAGE PROCESSING APPARATUS AND MEDICAL IMAGE PROCESSING METHOD

CROSS-REFERENCE TO RELATED APPLICATION

This application is based upon and claims the benefit of priority from Japanese Patent Application No. 2010-207207, filed on Sep. 15, 2010, the entire contents of which are incorporated herein by reference.

FIELD

The embodiment of the present invention relates to a medical image processing apparatus and a medical image processing method which can accurately diagnose ischemic heart disease caused by a stenosis in a vessel or the like.

BACKGROUND

Medical image diagnosis has rapidly advanced by X-ray CT (Computed Tomography) apparatuses and MRI (Magnetic Resonance Imaging) apparatuses which have been put to practical use with recent developments in computer technology, and has thereby become indispensable in current medical care. In particular, in the X-ray CT apparatuses and the MRI apparatuses, biological information detecting units, arithmetic processing units or the like have been improved in processing speed and performance, so that image data can be displayed in real time. Furthermore, three-dimensional image information (volume data) can be more easily collected, and three-dimensional image data and MPR (Multi Planar Reconstruction) image data can be more easily generated/displayed by using the volume data. Thus, it becomes possible to accurately detect a stenosis site in a coronary artery of a patient having ischemic heart disease (referred to as object below), and accurately measure a rate of stenosis thereof, for example.

The ischemic heart disease such as myocardial infarction is mainly caused by a stenosis in a coronary artery. Thus, in a conventional case, a stenosis site in a coronary artery is detected and a rate of stenosis thereof is measured by use of morphological image data such as two-dimensional image data and three-dimensional image data obtained by administering a contrast agent into coronary arteries. A stenosis site having a relatively high rate of stenosis among the detected stenosis sites is determined as a cause of myocardial infarction, and subjected to intravascular treatment such as PCI (Percutaneous Coronary Intervention) in which an intravascular device such as a stent is placed in the stenosis site.

However, myocardial infarction may sometimes not develop even when there is a stenosis site in a coronary artery. There has been a report that a patient has a favorable prognosis when given medication therapy as compared to a patient given the PCI depending on a degree of ischemia in myocardial tissue. Thus, evaluation of a stenosis site with respect to an ischemic region in myocardial tissue is considered as important in order to determine a course of treatment for the stenosis site.

In response to such requirements, a medical image diagnosis apparatus or a medical image processing apparatus has been proposed which processes time-series volume data collected from a cardiac region of an object into which a contrast agent is administered, and thereby generates/displays functional image data such as myocardial perfusion image data in which an ischemic region in myocardial tissue can be identified.

Separate collection modes of image data are respectively employed to collect the morphological image data to detect a stenosis site in a coronary artery and measure a rate of stenosis, and to collect the functional image data to identify or measure an ischemic region. Attending doctors of the object subjectively analyze information on the stenosis site and information on the ischemic region obtained in the respective collection modes based on their experiences, and judge a relationship between the ischemic region and the stenosis site.

In recent years, a method of synthesizing an ischemic region in functional image data on morphological image data of a cardiac region including a stenosis site in a coronary artery and displaying the obtained image data has been also developed. In this case, however, the attending doctors also make a subjective judgment based on their experiences by observing the respective image data. With the aforementioned conventional methods, the relationship between the ischemic region and the stenosis site cannot be accurately determined. It is thus difficult to determine a preferable course of treatment for the stenosis site.

BRIEF DESCRIPTION OF THE DRAWINGS

In accompanying drawings.

Figure 7:
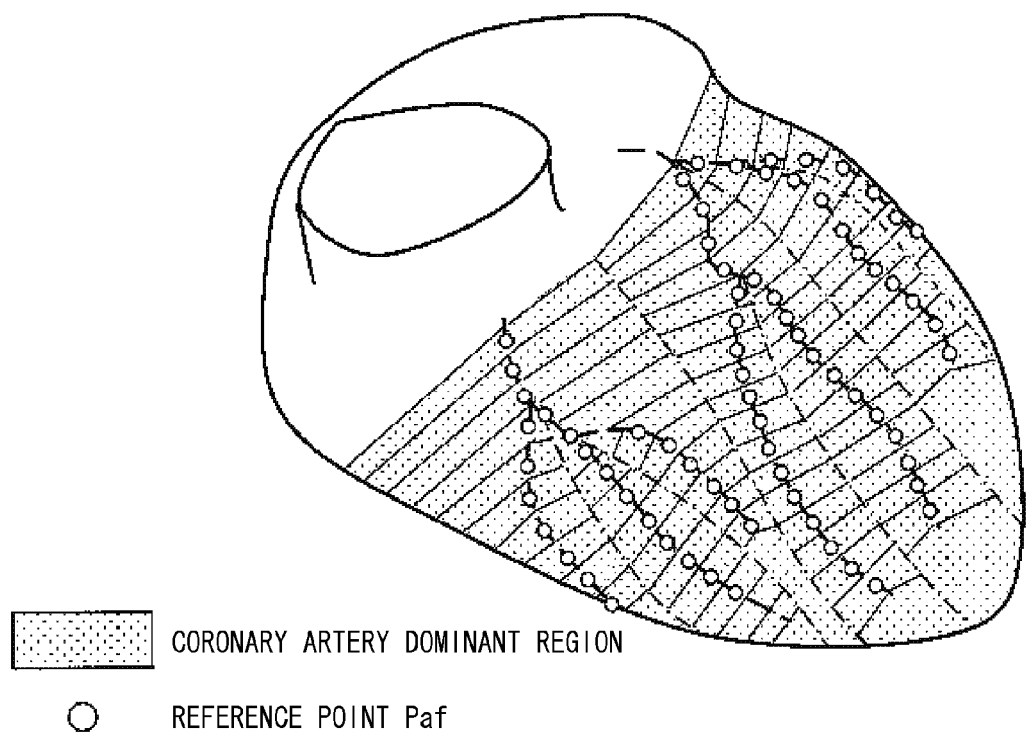
Figure 8:
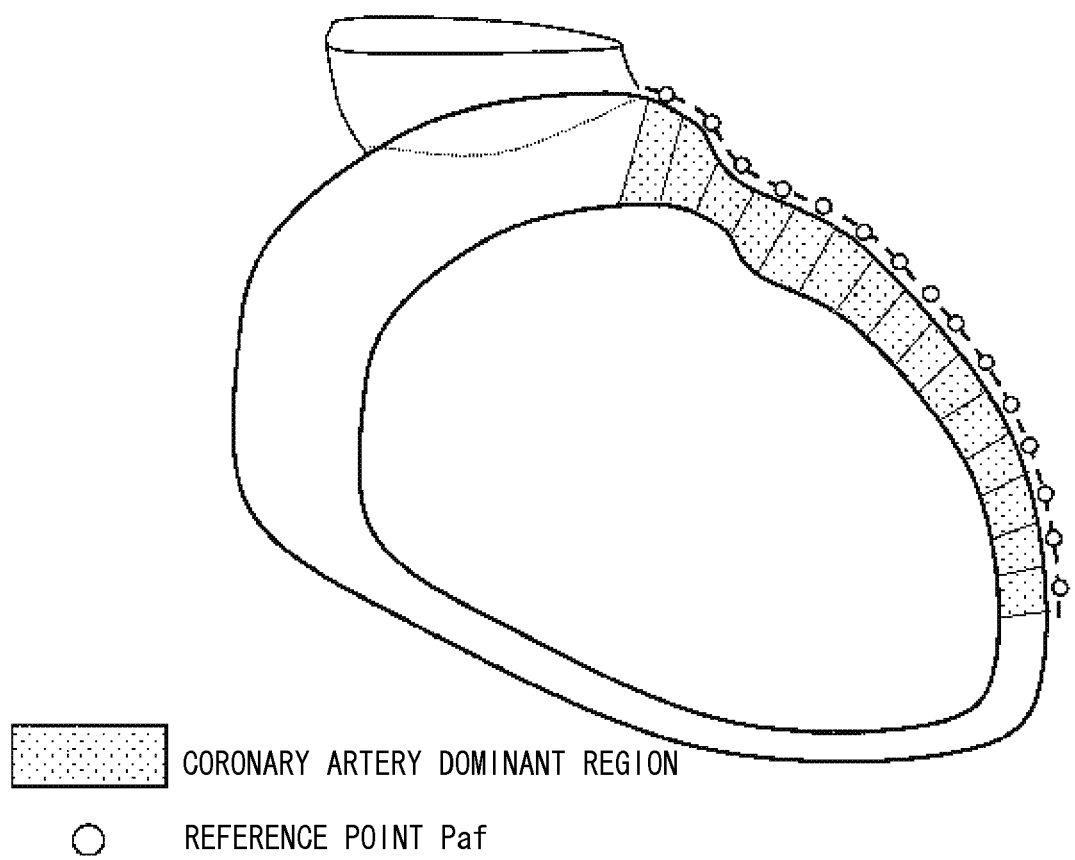
Figure 9:
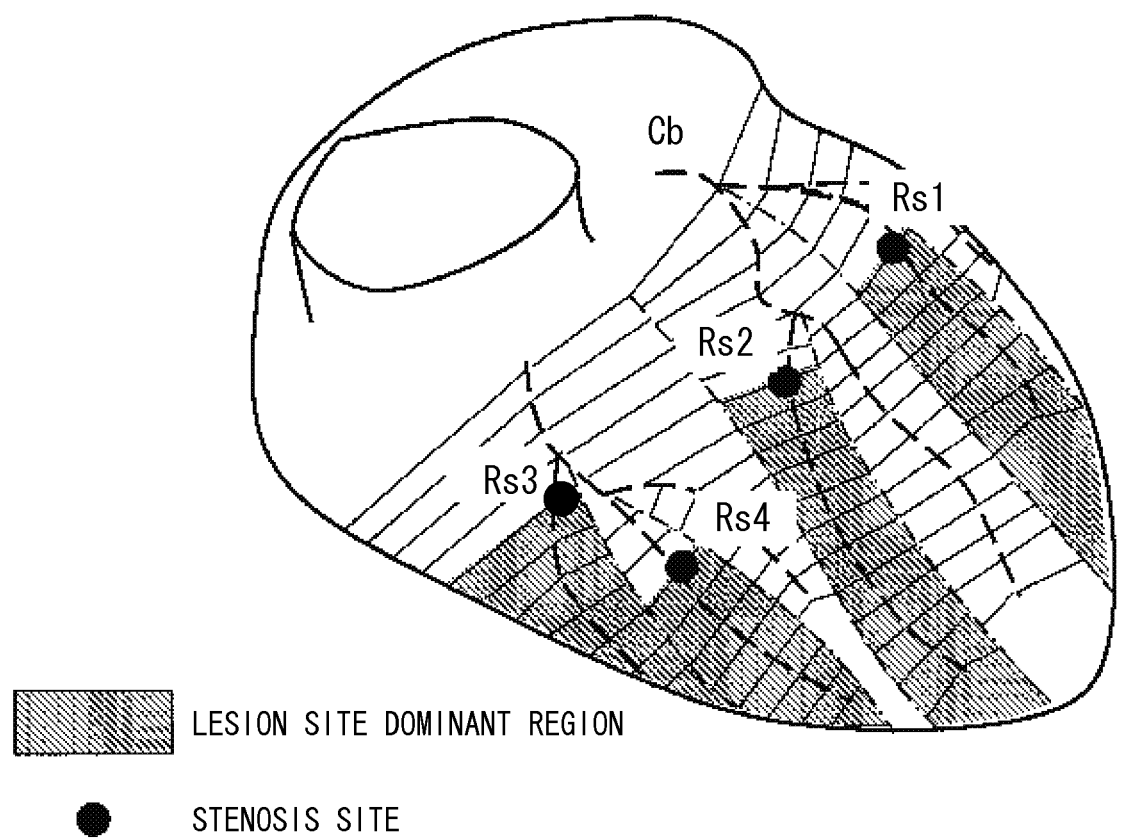
Figure 10:
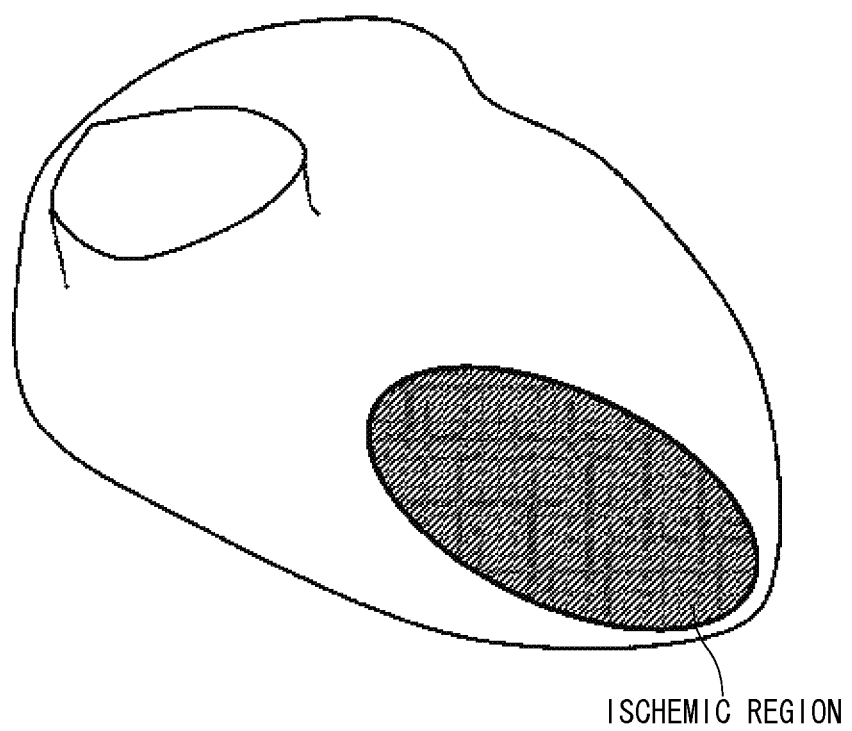
Figure 11:
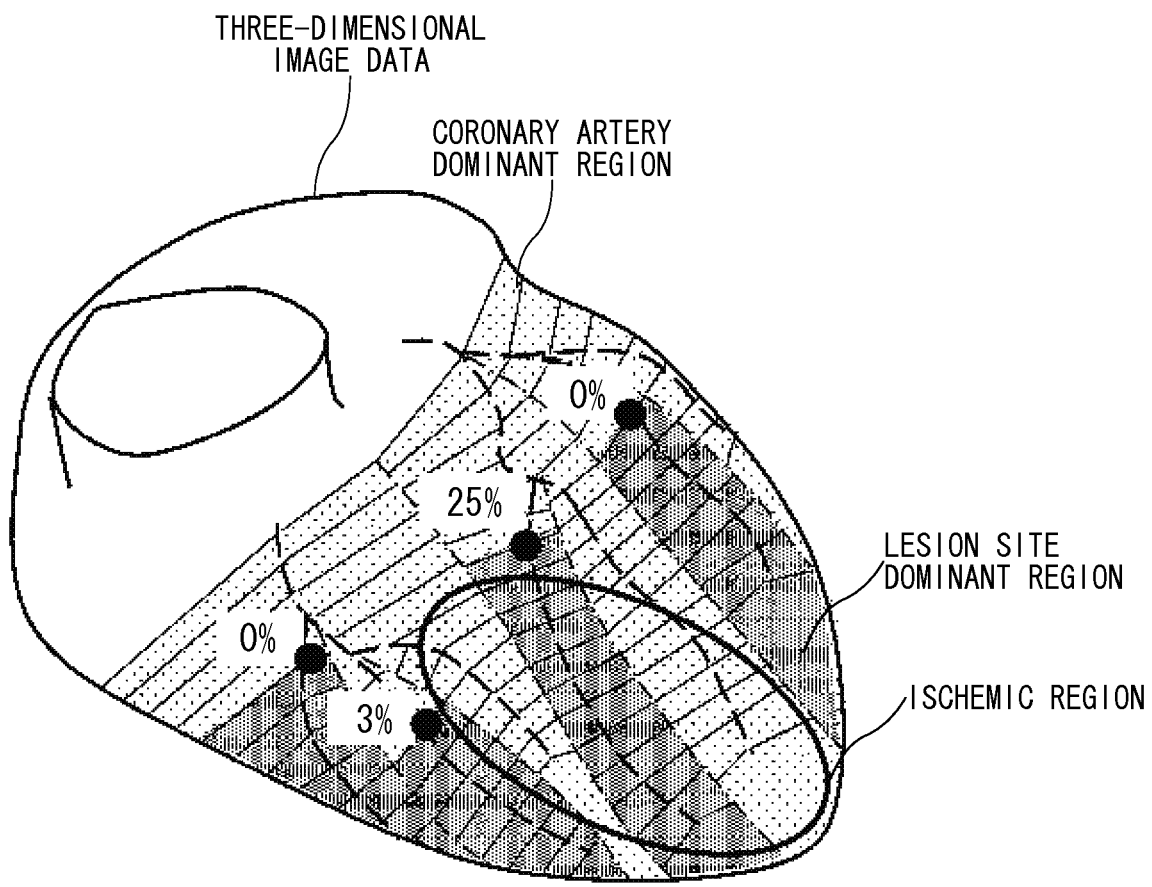
Figure 12:
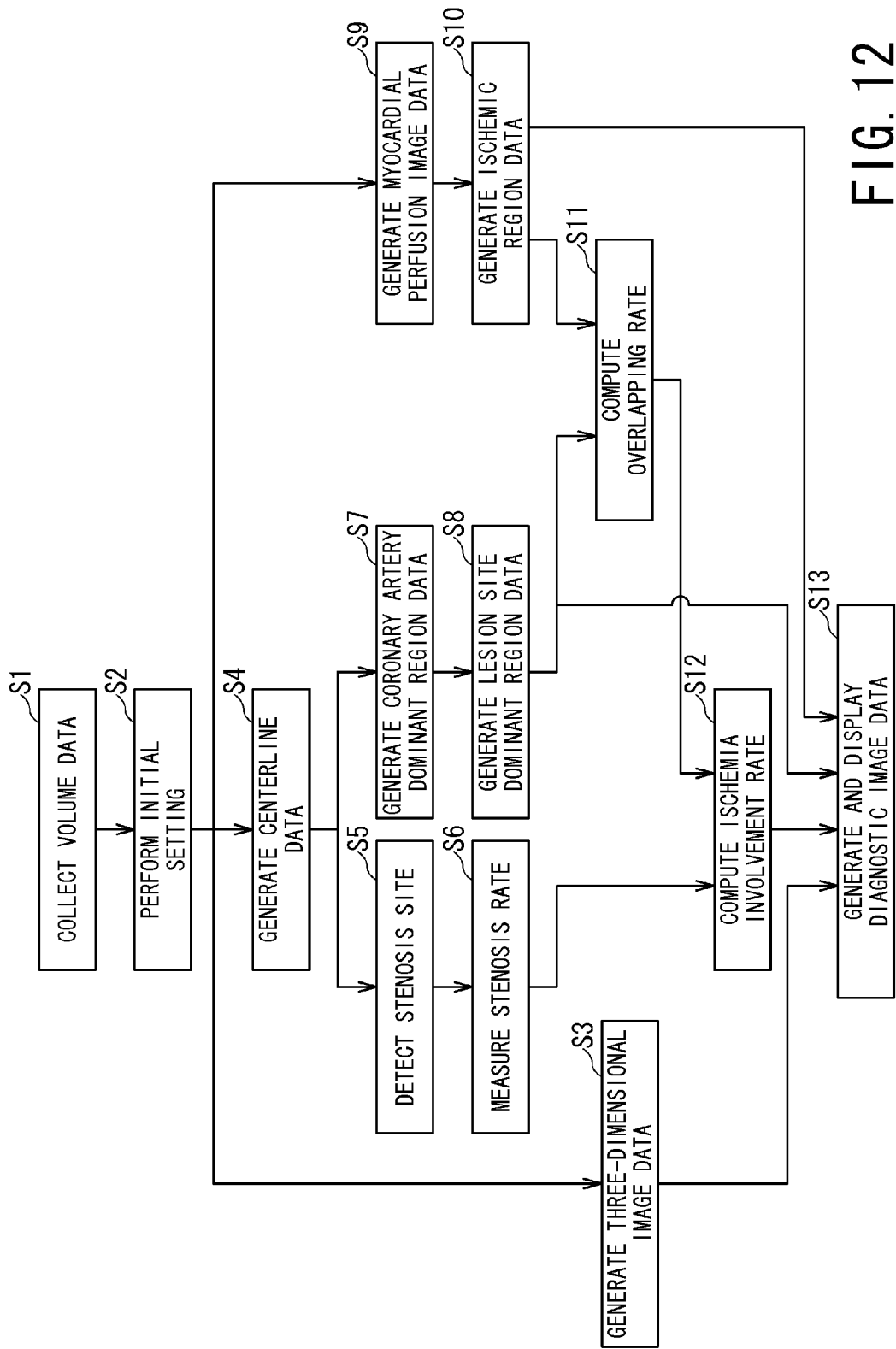
Figure 13:
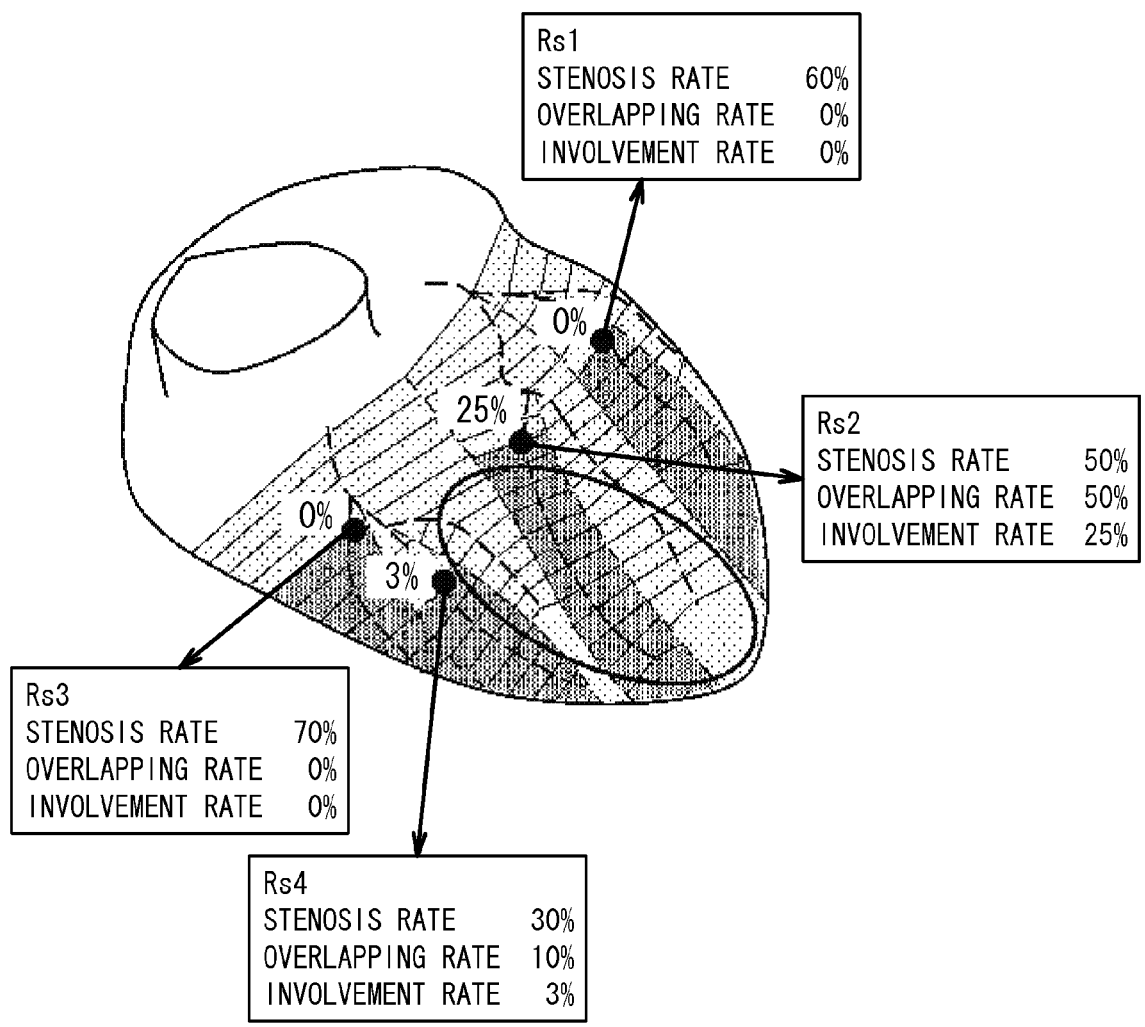
Figure 14:
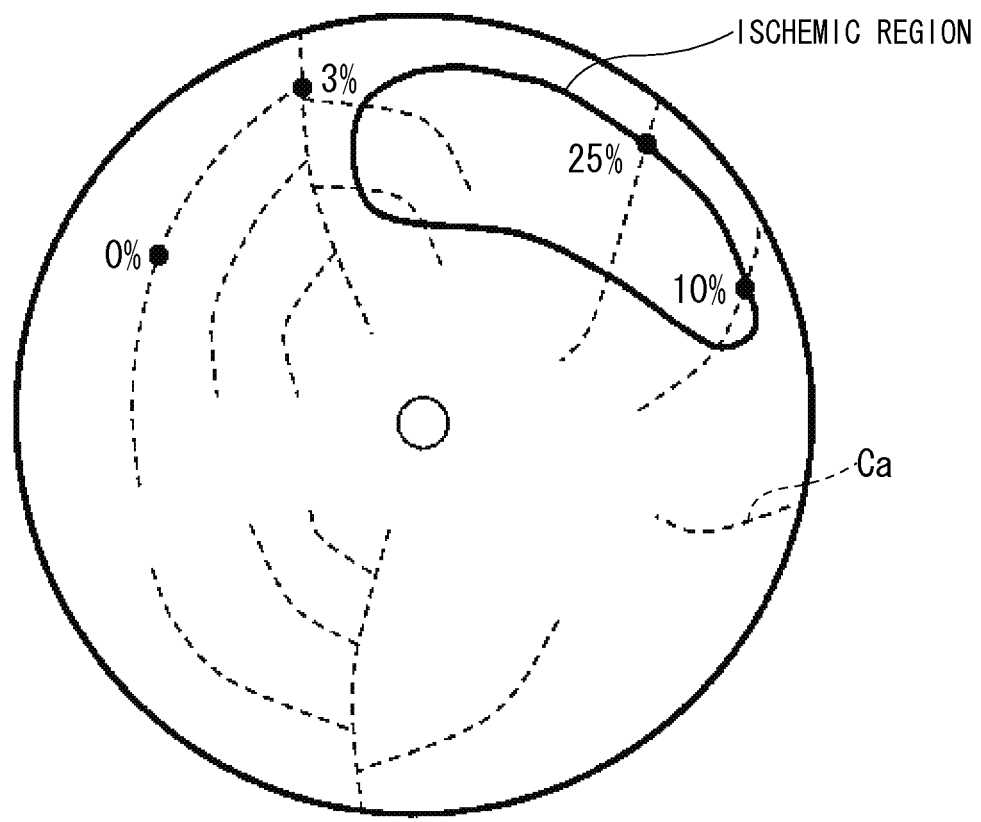

each of FIGS. 6A to 6D is a schematically diagram illustrating a dilation process aimed at generating coronary artery dominant region data according to the present embodiment;

FIG. 7 is a diagram illustrating a specific example of the coronary artery dominant region data generated by the coronary artery dominant region data generating unit according to the present embodiment;

FIG. 8 is a diagram to explain a dilation process along a thickness direction of a myocardial region by the coronary artery dominant region data generating unit according to the present embodiment;

FIG. 9 is a diagram illustrating a specific example of a lesion site dominant region data generated by a lesion site dominant region data generating unit according to the present embodiment;

FIG. 10 is a diagram illustrating a specific example of an ischemic region data generated by an ischemic region generating unit according to the present embodiment;

FIG. 11 is a diagram illustrating a specific example of a diagnostic image data generated by a diagnostic image data generating unit according to the present embodiment;

FIG. 12 is a flowchart illustrating generation/display procedures of the diagnostic image data according to the present embodiment;

FIG. 13 is a diagram to explain clinical importance of an ischemia involvement rate shown in the diagnostic image data according to the present embodiment; and FIG. 14 is a diagram illustrating a diagnostic image data under a modified example of the present embodiment.

DETAILED DESCRIPTION

In the following, a medical image processing apparatus and a medical image processing method according to an embodiment of the present disclosure will be described by reference to the drawings.

To solve the above-described problems, the medical image processing apparatus according to the present embodiment has: a vessel running data generating unit configured to generate vessel running data of a vessel based on volume data collected by a medical image diagnosis apparatus; a lesion site detecting unit configured to detect positional information of a lesion site in the vessel based on the volume data; a vessel dominant region data generating unit configured to generate vessel dominant region data indicating a region dominated by the vessel in a region provided with nutrition based on the vessel running data; a lesion site dominant region data generating unit configured to generate lesion site dominant region data indicating a region dominated by the lesion site in the region provided with nutrition based on the vessel running data and the positional information of the lesion site; and a diagnostic image data generating unit configured to generate diagnostic image data by superimposing the vessel dominant region data and the lesion site dominant region data on morphological image data or functional image data generated based on the volume data.

To solve the above-described problems, the medical image processing method according to the present embodiment has: obtaining volume data collected by a medical image diagnosis apparatus from a storing unit; generating vessel running data of a vessel based on the obtained volume data; detecting positional information of a lesion site in the vessel based on the volume data; generating vessel dominant region data indicating a region dominated by the vessel in a region provided with nutrition based on the vessel running data; generating lesion site dominant region data indicating a region dominated by the lesion site in the region provided with nutrition based on the vessel running data and the positional information of the lesion site; generating diagnostic image data by superimposing the vessel dominant region data and the lesion site dominant region data on morphological image data or functional image data generated based on the volume data; and displaying the diagnostic image data on the display unit.

In the medical image processing apparatus according to the present embodiment described below, first, centerline data is generated on vessels, a lesion site is detected, and a degree of lesion is measured based on volume data of a predetermined heartbeat time phase. The volume data has been preliminarily collected from an object having disease in vessels. Three-dimensional vessel dominant region data and lesion site dominant region data are generated based on the volume data, the centerline data, and positional information of the lesion site. Subsequently, an ischemic region is extracted from functional image data that is generated based on time-series volume data. The time-series volume data have been preliminarily collected from the object. Three-dimensional ischemic region data is thereby generated. An involvement rate (an ischemia involvement rate) of the lesion site in the ischemic region is computed based on an overlapping rate of the ischemic region in the ischemic region data and a lesion site dominant region in the lesion site dominant region data, and the lesion degree. The vessel dominant region data, the lesion site dominant region data, and the ischemic region data are superimposed on three-dimensional morphological image data generated using the volume data. The computational result of the ischemia involvement rate is further added to a stenosis position or the vicinity thereof on the morphological image data. Accordingly, diagnostic image data is generated.

The embodiment described below employs a case in which myocardial perfusion image data is generated as the functional image data by accumulating the preliminarily-collected time-series volume data of a predetermined heartbeat time phase, and three-dimensional image data and MPR image data are generated as the morphological image data by rendering the volume data of a predetermined heartbeat time phase extracted from the time-series volume data. However, the morphological image data and the functional image data are not limited thereto.

Although a stenosis is employed as the lesion of the vessel, e.g. a coronary artery in the embodiment described below, the lesion may be spasm, occlusion, or plaque. The vessel is also not limited to the coronary artery, and may be a cerebral artery, for example. In this case, cerebral tissue is a region provided with nutrition from the cerebral artery.

(Configuration of Apparatus)

Figure 1:
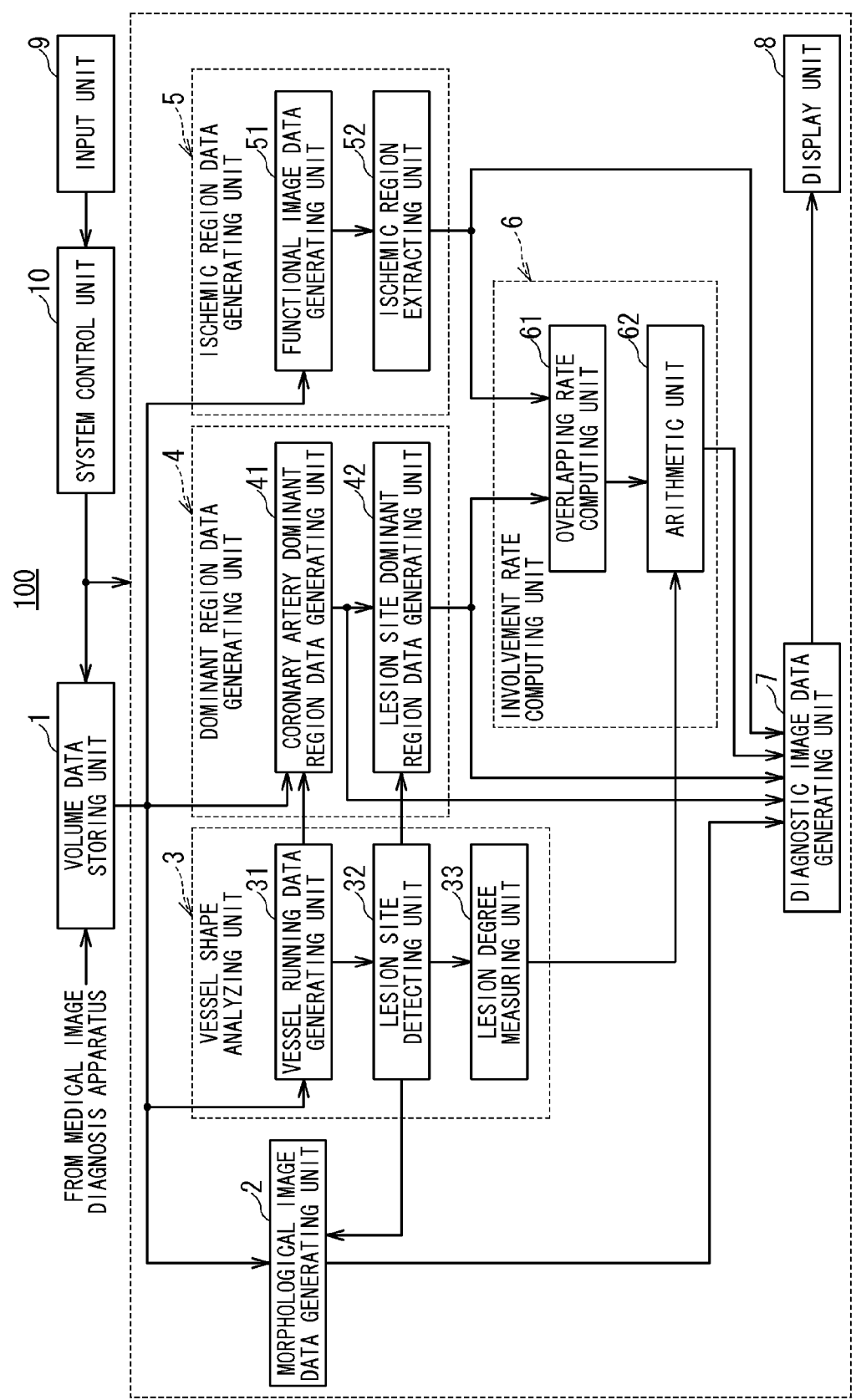
FIG. 1 is a block diagram illustrating an entire configuration of a medical image processing apparatus according to a present embodiment.
Figure 2:
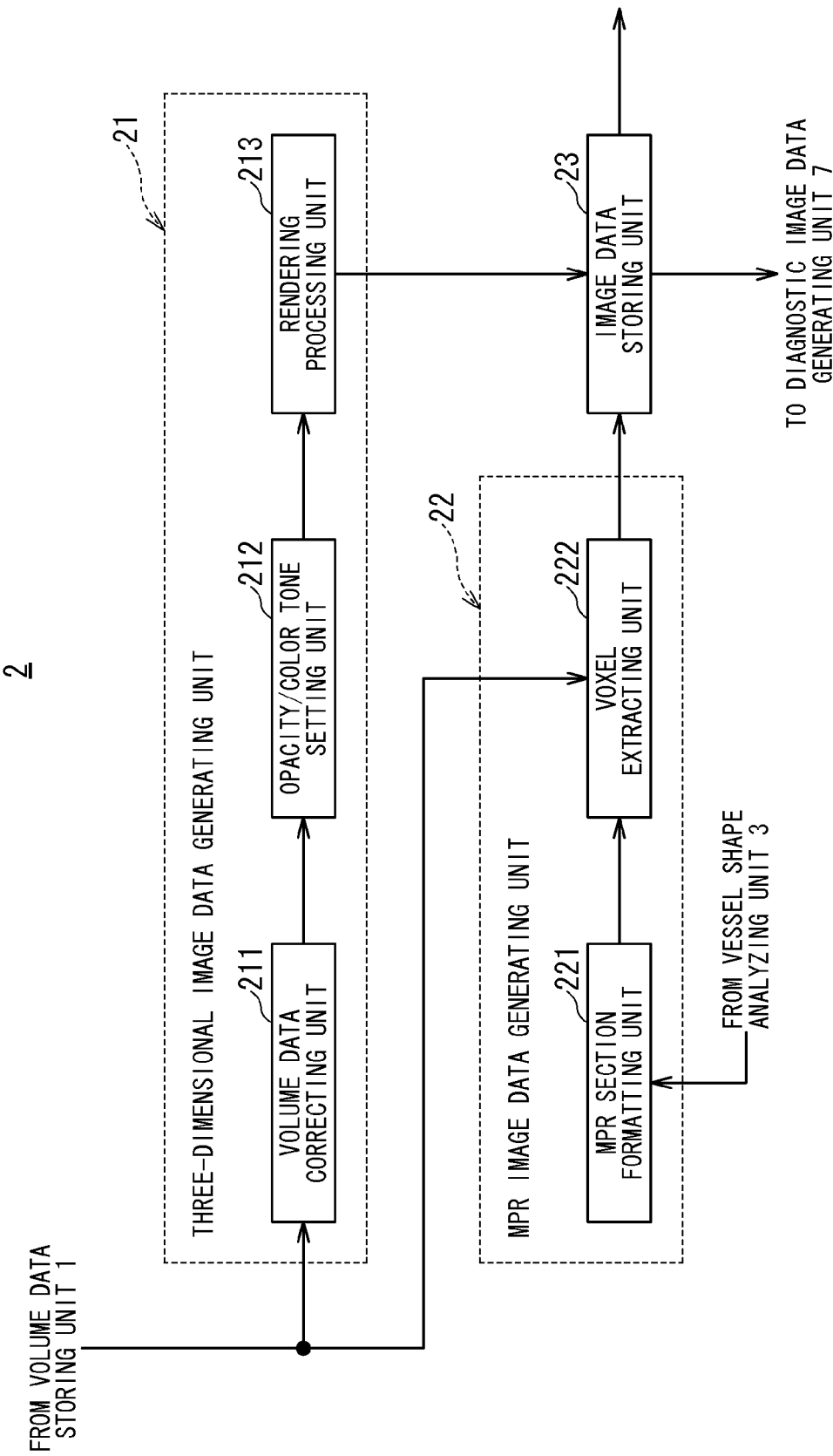
FIG. 2 is a block diagram illustrating a specific configuration of a morphological image data generating unit of the medical image processing apparatus according to the present embodiment.

In the following, a configuration and a function of the medical image processing apparatus according to the present embodiment will be described based on FIGS. 1 to 11. FIG. 1 is a block diagram illustrating an entire configuration of the medical image processing apparatus. FIG. 2 is a block diagram illustrating a specific configuration of a morphological image data generating unit of the medical image processing apparatus.

A medical image processing apparatus 100 according to the present embodiment shown in FIG. 1 includes: a volume data storing unit 1 configured to store three-dimensional image information (hereinafter "volume data") supplied from a separately-installed medical image diagnosis apparatus such as an X-ray CT apparatus and an MRI apparatus via a network or a storage medium (not shown); a morphological image data generating unit 2 configured to generate morphological image data such as three-dimensional image data and MPR image data of a cardiac region based on the volume data; a vessel shape analyzing unit 3 configured to generate vessel running data of a coronary artery, detect a stenosis site in the coronary artery, and measure a rate of stenosis based on the volume data; a dominant region data generating unit 4 configured to generate coronary artery dominant region data and lesion site dominant region data based on the volume data, the vessel running data and the detection result of the stenosis site; an ischemic region data generating unit 5 configured to generate functional image data indicating blood flow information returning through myocardial tissue based on the volume data, and generate ischemic region data of the myocardial tissue based on the functional image data; and an involvement rate computing unit 6 configured to compute an ischemia involvement rate of the stenosis site in an ischemic region based on the ischemic region data, the lesion site dominant region data and the measurement result of the stenosis rate.

The medical image processing apparatus 100 further includes: a diagnostic image data generating unit 7 configured to generate image data (hereinafter "diagnostic image data") for diagnosing ischemic disease based on the morphological image data, the coronary artery dominant region data, the lesion site dominant region data, the ischemic region data, and the computational result of the ischemia involvement rate or the like; a display unit 8 configured to display the obtained diagnostic image data; an input unit 9 configured to, for example, input object information, set threshold values, set image data generation conditions and region data generation conditions, select a stenosis site, and input various instruction signals; and a system control unit 10 configured to collectively control the above respective units.

The volume data storing unit 1 stores time-series volume data with a heartbeat time phase as additional information. The time-series volume data have been preliminarily collected by the medical image diagnosis apparatus (not shown) from a cardiac region of an object by administering a contrast agent into coronary arteries of the cardiac region, for example.

Next, a specific configuration of the morphological image data generating unit 2 will be described based on FIG. 2. The morphological image data generating unit 2 in FIG. 2 includes: a three-dimensional image data generating unit 21 configured to generate three-dimensional image data based on volume data of a predetermined heartbeat time phase read out from the volume data storing unit 1; an MPR image data generating unit 22 configured to generate MPR image data along a predetermined section based on the volume data; and an image data storing unit 23 configured to temporarily store the three-dimensional image data and the MPR image data. The three-dimensional image data generating unit 21 has a volume data correcting unit 211, an opacity/color tone setting unit 212, and a rendering processing unit 213.

The volume data correcting unit 211 corrects a voxel value of the volume data supplied from the volume data storing unit 1 based on an inner product value between a view vector for three-dimensional display and a normal vector to an organ boundary surface, which are preliminarily set. The opacity/color tone setting unit 212 sets an opacity and a color tone based on the corrected voxel value. The rendering processing unit 213 renders the volume data based on the opacity and the color tone set by the opacity/color tone setting unit 212. The three-dimensional image data is thereby generated.

The MPR image data generating unit 22 of the morphological image data generating unit 2 has an MPR section formatting unit 221 and a voxel extracting unit 222. The MPR section formatting unit 221 forms a planar or curved MPR section (a first MPR section) including centerline data within a predetermined range around a stenosis site based on vessel running data (that is, centerline data of a coronary artery described later) and positional information of a stenosis site supplied from the vessel shape analyzing unit 3. The MPR section formatting unit 221 also forms an MPR section (a second MPR section) including the stenosis site and perpendicular to the centerline data.

The voxel extracting unit 222 sets the first MPR section and the second MPR section formed by the MPR section formatting unit 221 with respect to the volume data of the predetermined heartbeat time phase read out from the volume data storing unit 1, and extracts voxels of the volume data existing on the MPR sections. The voxel extracting unit 222 thereby generates the MPR image data around the stenosis site. The three-dimensional image data generated in the three-dimensional image data generating unit 21 and the MPR image data generated in the MPR image data generating unit 22 are temporarily stored in the image data storing unit 23, and supplied to the diagnostic image data generating unit 7 as the morphological image data. The MPR image data is generated and displayed with respect to one or a plurality of stenosis sites with a high ischemia involvement rate selected in the input unit 9, for example.

Returning to FIG. 1, the vessel shape analyzing unit 3 includes: a vessel running data generating unit 31 configured to generate the centerline data of a coronary artery as the vessel running data; a lesion site detecting unit 32 configured to detect the positional information of a stenosis site in the coronary artery; and a lesion degree measuring unit 33 configured to measure a stenosis rate of the stenosis site. The vessel running data generating unit 31 has a vascular region detecting unit and a centerline data generating unit (not shown).

The vascular region detecting unit of the vessel running data generating unit 31 compares voxel values of the volume data of the predetermined heartbeat time phase read out from the volume data storing unit 1 with a preliminarily-set threshold value $\alpha$, and extracts a voxel having a larger voxel value than the threshold value $\alpha$ by administering a contrast agent. The vascular region detecting unit thereby detects a vascular region of the coronary artery.

The centerline data generating unit of the vessel running data generating unit 31 sets a reference point (a first reference point) inside the vascular region detected by the vascular region detecting unit, and generates the centerline data with the reference point as an origin. For example, a plurality of unit vectors are generated in all three-dimensional angular directions from the reference point that is arranged at any position in the vascular region. A unit vector in a direction with a largest distance to a boundary surface of the vascular region is selected as a search vector out of the unit vectors. Coordinates of a center position of a vessel cross section perpendicular to the search vector are computed. A new search vector whose direction is corrected such that an intersecting position of the search vector and the vessel cross section corresponds to the center of the vessel cross section is set in the center of the vessel cross section. The above procedures are repeated by use of the corrected search vector, to obtain a plurality of center position coordinates in a vessel running direction. The centerline data of the coronary artery is thereby generated based on the plurality of center position coordinates.

Figure 3:
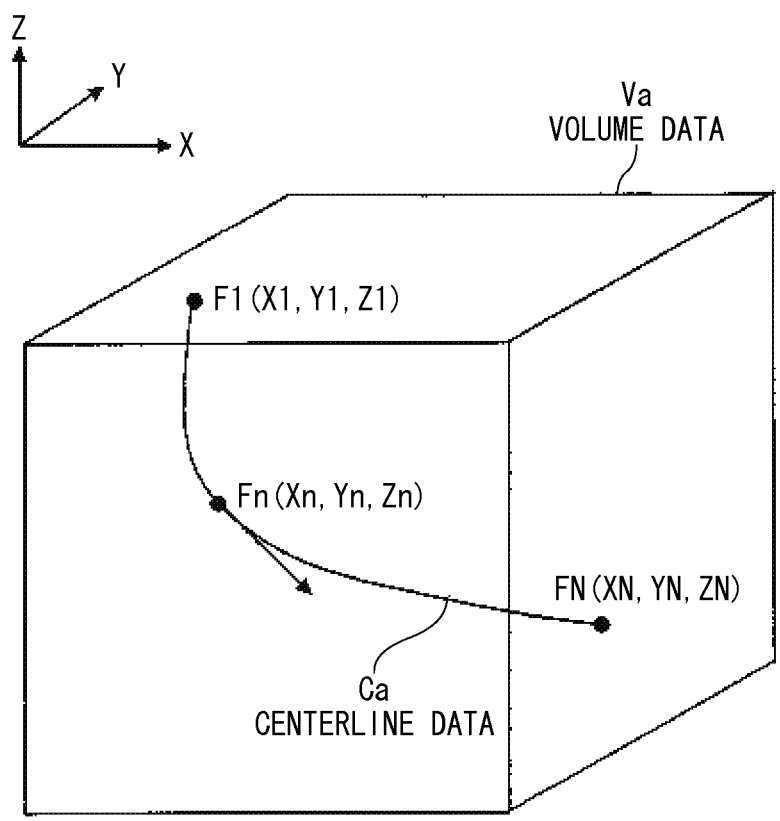
FIG. 3 is a diagram to explain centerline data generated by a centerline data generating unit according to the present embodiment.

FIG. 3 shows a coordinate system of centerline data Ca generated by the centerline data generating unit with respect to volume data Va. The volume data Va is constituted by a plurality of voxels that are arrayed in a three-dimensional region. The centerline data Ca is generated by connecting a coordinate F1 (X1, Y1, Z1) as an origin and a coordinate FN (XN, YN, ZN) as an end through a center Fn (Xn, Yn, Zn) in a cross section of an intravascular lumen in the volume data Va.

Returning to FIG. 1 again, the lesion site detecting unit 32 of the vessel shape analyzing unit 3 detects the positional information of the stenosis site in the coronary artery based on the vascular region data of the coronary artery supplied from the vascular region detecting unit and the centerline data of the coronary artery supplied from the centerline data generating unit. The lesion degree measuring unit 33 measures the stenosis rate of the stenosis site by comparing a cross sectional area of the coronary artery in the stenosis site detected by the lesion site detecting unit 32 with a cross sectional area of a normal coronary artery.

Figure 4:
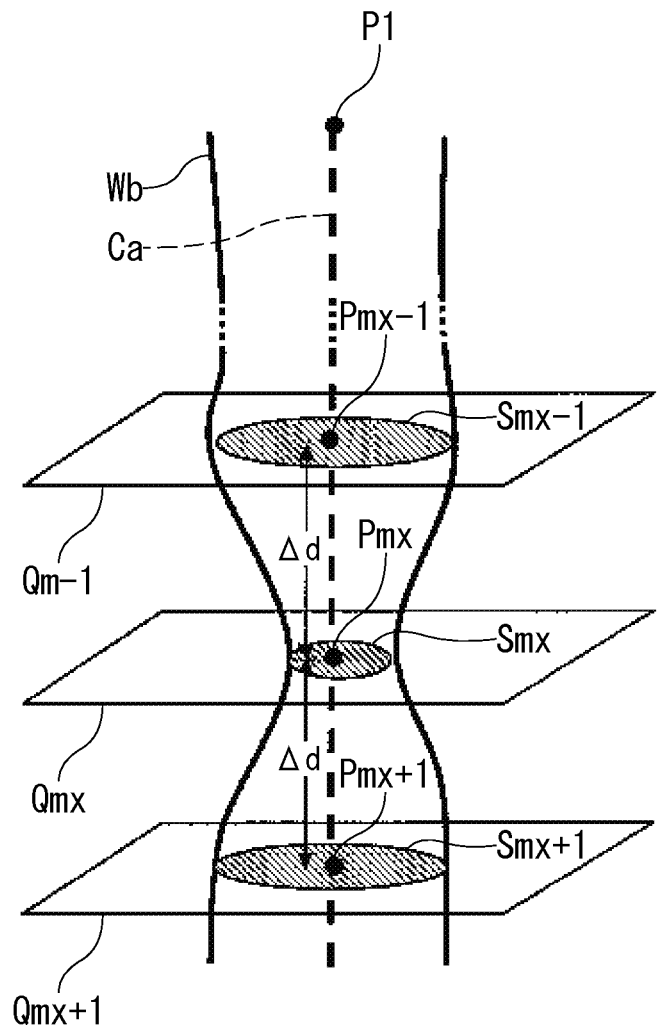
FIG. 4 is a diagram illustrating a method for detecting a lesion site by a lesion site detecting unit according to the present embodiment and a method for measuring a lesion degree by a lesion degree measuring unit according to the present embodiment.

Next, a method for detecting the stenosis site in the coronary artery and a method for measuring the stenosis rate of the stenosis site will be described based on FIG. 4. Although FIG. 4 shows the detection of the stenosis site and the measurement of the stenosis rate with respect to a linearly-running coronary artery for the simplicity of illustration, the detection of the stenosis site and the measurement of the stenosis rate may be also performed on a curved coronary artery by the same procedures.

In this case, the lesion site detecting unit 32 receives the vascular region data of the coronary artery supplied from the vascular region detecting unit of the vessel running data generating unit 31 and the centerline data of the coronary artery supplied from the centerline data generating unit thereof. The lesion site detecting unit 32 arranges M reference points Pm (m=1 to M) (second reference points) on the centerline data Ca at a predetermined interval Δd as shown in FIG. 4, for example. The lesion site detecting unit 32 then sets sections Qm (m=1 to M) respectively including the reference points Pm and substantially perpendicular to the centerline data Ca. The lesion site detecting unit 32 measures an intersecting sectional area between vascular region data Wb of the coronary artery and each of the sections Qm as a cross sectional area Sm (m=1 to M) of the coronary artery at each of the reference points Pm. The lesion site detecting unit 32 detects a stenosis site (for example, Pm=Pmx) whose cross sectional area Sm obtained as described above has a smaller value than a predetermined threshold value β.

Figure 5:
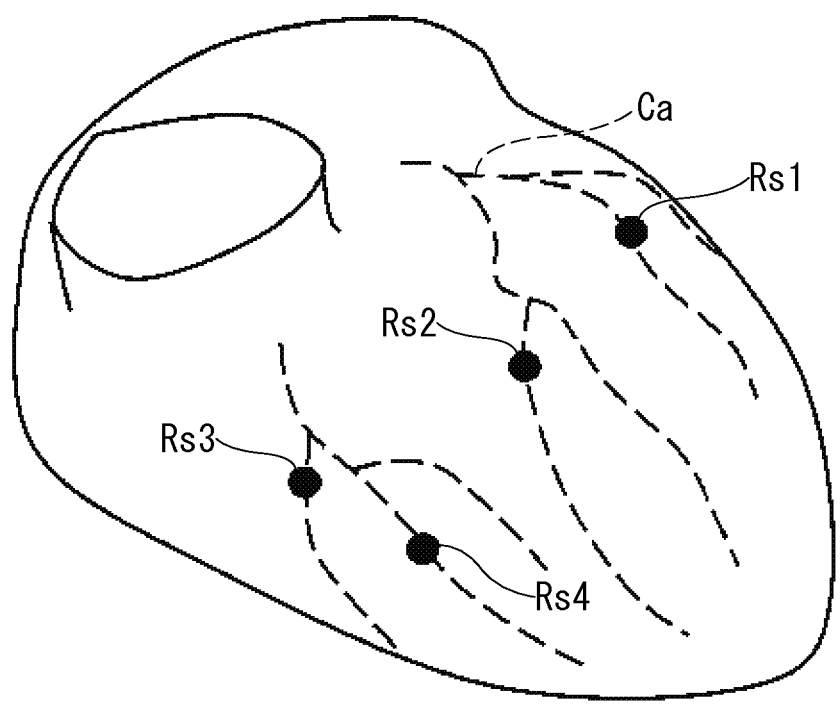
FIG. 5 is a diagram illustrating a specific example of the lesion site detected by the lesion site detecting unit according to the present embodiment.

A specific example of the stenosis site detected by the lesion site detecting unit 32 is shown in FIG. 5. In FIG. 5, stenosis sites Rs1 to Rs4 detected by the lesion site detecting unit 32 are superimposed on the centerline data Ca of the coronary artery generated by the centerline data generating unit of the vessel running data generating unit 31. Although the following description is made based on the stenosis sites, the positions and the number of stenosis sites are not limited thereto.

The lesion degree measuring unit 33 measures an average cross sectional area Sav by averaging all or some (for example, a plurality of cross sectional areas in the vicinity of the stenosis site Pmx) of the cross sectional areas Sm (m=1 to M) of the coronary artery measured at the reference points Pm by the lesion site detecting unit 32. The lesion degree measuring unit 33 substitutes a cross sectional area Smx of the stenosis site Pmx and the average cross sectional area Sav into a following expression (1), and thereby measures a stenosis rate Rmx of the stenosis site Pmx.

$$Rmx = \frac{Sav - Smx}{Sav} \quad (1)$$

Next, the dominant region data generating unit 4 in FIG. 1 includes a coronary artery dominant region data generating unit (a vessel dominant region data generating unit) 41 configured to generate three-dimensional coronary artery dominant region data indicating a region dominated by coronary arteries in myocardial tissue (a region provided with the nutrient from vessel) (more specifically, a region of the myocardial tissue to which blood is supplied through the coronary arteries), and a lesion site dominant region data generating unit 42 configured to generate three-dimensional lesion site dominant region data indicating a region dominated by a stenosis site in a coronary artery (more specifically, a region of the myocardial tissue in an ischemic state due to blood blockage in the stenosis site).

The coronary artery dominant region data generating unit 41 has a myocardial region extracting unit (not shown). The myocardial region extracting unit extracts a myocardial tissue region (a myocardial region) by, for example, binarizing the volume data of the predetermined heartbeat time phase read out from the volume data storing unit 1, and thereby generates three-dimensional myocardial region data. Subsequently, the coronary artery dominant region data generating unit 41 sets F reference points Paf (f=1 to F) (third reference points) at a predetermined interval Δe on the three-dimensional centerline data supplied from the vessel running data generating unit 31 of the vessel shape analyzing unit 3. The coronary artery dominant region data generating unit 41 generates the coronary artery dominant region data constituted by regions dominated by the respective reference points Paf (referred to as segment dominant region below) based on the centerline data in which the reference points Paf are set, and the myocardial region data supplied from the myocardial region extracting unit.

To be more specific, the myocardial region data and the centerline data are synthesized. The reference points Paf set on the three-dimensional centerline data at the predetermined interval Δe are projected onto a surface of the three-dimensional myocardial region. A reference voxel Gf (f=1 to F) on the myocardial tissue surface corresponding to each of the reference points Paf is thereby detected. Voxels included in the myocardial region are subjected to a dilation process from each of the obtained reference voxels Gf. The three-dimensional coronary artery dominant region data is thereby generated.

Figure 6A:
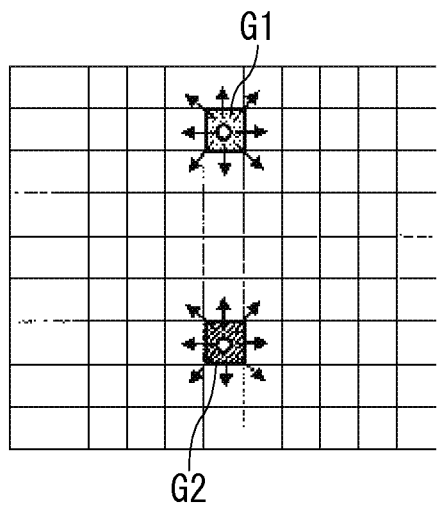
Figure 6B:
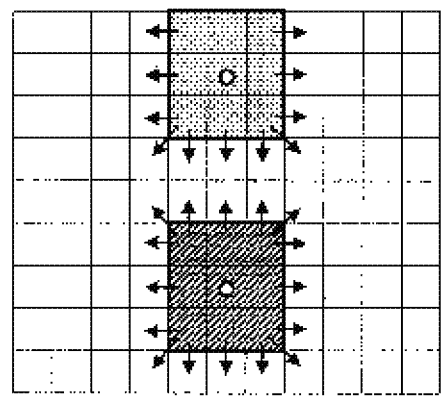
Figure 6C:
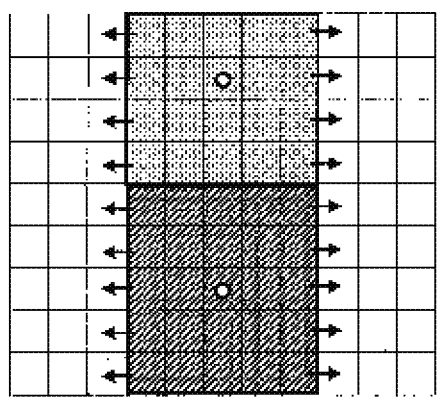
Figure 6D:
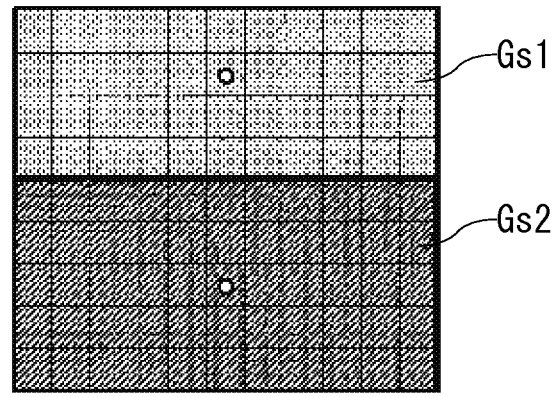

FIGS. 6A to 6D schematically show the dilation process applied to generate the coronary artery dominant region data. FIG. 6A shows a myocardial region in which reference voxels G1 and G2 are set on its surface by projecting reference points Pa1 and Pa2 (not shown). FIGS. 6B and 6C show segment dominant regions sequentially formed by the dilation process in directions indicated by arrows respectively from the reference voxels G1 and G2. FIG. 6D shows segment dominant regions Gs1 and Gs2 finally formed by the dilation process.

To be more specific, in FIG. 6B, voxels adjacent to the reference voxels G1 and G2 are connected together by the dilation process. In FIG. 6C, the same dilation process is repeated on voxels adjacent to the voxels connected together by the dilation process in FIG. 6B. All the voxels in the myocardial region are subjected to the dilation process from any of the reference voxels Gf (f=1 to F). Accordingly, the three-dimensional coronary artery dominant region data constituted by segment dominant regions Gsf respectively corresponding to the reference points Paf is generated as shown in FIG. 7. A dashed line shown in FIG. 7 indicates the centerline data of the coronary artery. The reference points Paf are set on the centerline data at the predetermined interval Δe.

Although the case in which the voxels existing on the surface of the myocardial region are subjected to the dilation process is shown in FIGS. 6A to 6D, the dilation process is actually also applied to voxels inside the myocardial region respectively from the reference voxels Gf. The three-dimensional coronary artery dominant region data is thereby generated as shown in FIG. 7. In this case, a thickness direction of the myocardial region is segmented perpendicular to the surface as shown in FIG. 8. This is because a thin coronary artery (Transmural Coronary Artery) branched from a relatively thick coronary artery (Epicardial Coronary Artery) running on the surface of the myocardial tissue normally runs in a direction substantially perpendicular to the thick coronary artery to feed blood into the myocardial tissue.

Next, the lesion site dominant region data generating unit 42 of the dominant region data generating unit 4 shown in FIG. 1 receives the positional information of the stenosis site supplied from the lesion site detecting unit 32 of the vessel shape analyzing unit 3, and extracts a reference point corresponding to the stenosis site from the reference points Paf (f=1 to F) set on the centerline data. The lesion site dominant region data generating unit 42 further extracts all the reference points set on a downstream side (a lower right direction in FIG. 7) of the extracted reference point from the reference points Paf (f=1 to F). The lesion site dominant region data generating unit 42 synthesizes a plurality of segment dominant regions formed by the coronary artery dominant region data generating unit 41 with respect to the obtained respective reference points, and thereby generates the three-dimensional lesion site dominant region data. FIG. 9 shows a specific example of the lesion site dominant region data generated by the lesion site dominant region data generating unit 42. Lesion site dominant regions of the stenosis sites Rs1 to Rs4 shown in FIG. 5 are indicated by diagonal lines.

Next, the ischemic region data generating unit 5 shown in FIG. 1 includes a functional image data generating unit 51 configured to generate myocardial perfusion image data obtained by imaging blood flow information in myocardial tissue as the functional image data, and an ischemic region extracting unit 52 configured to generate ischemic region data by extracting an ischemic region from the obtained myocardial perfusion image data.

The functional image data generating unit 51 extracts a plurality of volume data of a predetermined heartbeat time phase based on a time point when the contrast agent is administered from the time-series volume data preliminarily stored in the volume data storing unit 1. The functional image data generating unit 51 accumulates the volume data, for example, to generate the myocardial perfusion image data.

The ischemic region extracting unit 52 compares voxel values of the myocardial perfusion image data with a predetermined threshold value $\gamma$. The myocardial perfusion image data is generated by the functional image data generating unit 51 based on the volume data of the object. The ischemic region extracting unit 52 thereby extracts a region with a smaller voxel value than the threshold value $7\gamma$ as indicated by a diagonal line portion in FIG. 10, for example, (that is, a region in which a blood flow rate into the myocardial tissue is smaller than a predetermined value) as the ischemic region. The ischemic region extracting unit 52 generates the three-dimensional ischemic region data based on the extraction result.

Next, the involvement rate computing unit 6 in FIG. 1 has a function to compute an involvement rate of the stenosis site in the ischemic region indicated in the ischemic region data. The involvement rate computing unit 6 includes an overlapping rate computing unit 61 and an arithmetic unit 62.

The overlapping rate computing unit 61 computes an overlapping rate of the three-dimensional lesion site dominant region data supplied from the lesion site dominant region data generating unit 42 of the dominant region data generating unit 4 and the three-dimensional ischemic region data supplied from the ischemic region extracting unit 52 of the ischemic region data generating unit 5. For example, when the lesion site dominant region in the lesion site dominant region data is Ba and the ischemic region in the ischemic region data is Bb, an overlapping rate Ax is computed by a following expression (2) that is preliminarily set.

$$Ax(\%) = \frac{Ba \cap Bb}{Ba \cup Bb} \times 100 \qquad (2)$$

(Ba∩Bb) shown in the expression (2) represents a common region of the lesion site dominant region and the ischemic region, and (Ba∪Bb) represents a region belonging to at least one of the lesion site dominant region and the ischemic region.

The arithmetic unit 62 of the involvement rate computing unit 6 has a function to compute the ischemia involvement rate that represents a possibility that each of the stenosis sites in the coronary arteries is involved in the ischemic region of the ischemic region data. More specifically, the arithmetic unit 62 computes the ischemia involvement rate of each stenosis site by multiplying the overlapping rate of the lesion site dominant region and the ischemic region by the stenosis rate. The overlapping rate is supplied with respect to each stenosis site from the overlapping rate computing unit 61, and the stenosis rate is supplied with respect to each stenosis site from the lesion degree measuring unit 33 of the vessel shape analyzing unit 3.

Next, the diagnostic image data generating unit 7 receives the three-dimensional coronary artery dominant region data and lesion site dominant region data generated in the dominant region data generating unit 4 and the three-dimensional ischemic region data generated in the ischemic region data generating unit 5. The diagnostic image data generating unit 7 subsequently superimposes the above various region data on the three-dimensional image data supplied from the morphological image data generating unit 2, and adds thereto the computational result of the ischemia involvement rate supplied with respect to each stenosis site from the involvement rate computing unit 6. The diagnostic image data is thereby generated.

FIG. 11 shows a specific example of the diagnostic image data generated by the diagnostic image data generating unit 7. As described above, the diagnostic image data is generated based on the three-dimensional image data as the morphological image data, the coronary artery dominant region data, the lesion site dominant region data and the ischemic region data superimposed on the three-dimensional image data, and the computational result of the ischemia involvement rate added to the region data.

In this case, the computational result of the ischemia involvement rate with respect to each stenosis site is arranged at a position where the stenosis site exists or the vicinity thereof. To clarify a relationship between the computational result and the stenosis site, a marker and centerline data indicating the position of the stenosis site as shown in FIG. 11 may be further added to generate the diagnostic image data. When an instruction signal to display the MPR image data, and a signal to select a stenosis site, MPR image data of which is to be displayed, are input into the input unit 9, the MPR image data generated by the MPR image data generating unit 22 of the morphological image data generating unit 2 is added to the above diagnostic image data with respect to the selected stenosis site.

Next, the display unit 8 in FIG. 1 has a function to display the diagnostic image data generated by the diagnostic image data generating unit 7. The display unit 8 includes a display data generating unit, a conversion unit and a monitor (not shown), for example. The display data generating unit generates display data by adding additional information such as object information and image data generation conditions to the diagnostic image data supplied from the diagnostic image data generating unit 7. The conversion unit performs a conversion process such as D/A conversion and television format conversion on the display data generated by the display data generating unit, and displays the converted data on the monitor.

The input unit 9 includes various input devices such as a keyboard, a switch, a selection button and a mouse, and a display panel (not shown). The input unit 9 thereby allows input of the object information, setting of the threshold values α, β, and γ, setting of the image data generation conditions and region data generation conditions, selection of the stenosis site, MPR image data of which is to be displayed, and input of various instruction signals. The input unit 9 and the display unit 8 are combined to form an interactive interface.

The system control unit 10 includes a CPU and a storing unit such as a memory (not shown). The memory stores various information input/set/selected in the input unit 9. The CPU collectively controls the respective units of the medical image processing apparatus 100 based on the information, to generate the morphological image data, the coronary artery dominant region data, the lesion site dominant region data and the ischemic region data, and compute the ischemia involvement rate. The CPU further controls the respective units to generate and display the diagnostic image data based on the above data.

(Generation/Display Procedures of the Diagnostic Image Data)

Next, generation/display procedures of the diagnostic image data according to the present embodiment will be described based on a flowchart in FIG. 12.

Before generating the diagnostic image data of the object having ischemic heart disease, a doctor (hereinafter "operator") who operates the medical image processing apparatus 100 stores the time-series volume data supplied from the separately-installed medical image diagnosis apparatus via a network or the like in the volume data storing unit 1 (step S1 in FIG. 12). The operator then inputs the object information, sets the threshold values α, β, and γ, and sets the image data generation conditions and the region data generation conditions, and thereafter inputs an instruction signal for starting the generation of the diagnostic image data in the input unit 9 (step S2 in FIG. 12). The information input or set in the above initial setting is stored in the storing unit of the system control unit 10.

The three-dimensional image data generating unit 21 of the morphological image data generating unit 2 receives the above instruction signal via the system control unit 10. The three-dimensional image data generating unit 21 thereby corrects the voxel value of the volume data of the predetermined heartbeat time phase read out from the volume data storing unit 1 based on the inner product value between the view vector for three-dimensional display and the normal vector to the organ boundary surface which are preliminarily set. The three-dimensional image data generating unit 21 sets the opacity and the color tone based on the corrected voxel value. The three-dimensional image data generating unit 21 then renders the volume data based on the opacity and the color tone set as described above, to generate the three-dimensional image data (step S3 in FIG. 12).

The vessel running data generating unit 31 of the vessel shape analyzing unit 3 receives the instruction signal to start the generation of the diagnostic image data from the system control unit 10. The vessel running data generating unit 31 thereby compares the voxel values of the volume data of the predetermined heartbeat time phase read out from the volume data storing unit 1 with the threshold value α set in the initial setting in the step S2. The vessel running data generating unit 31 extracts the voxel having a larger voxel value than the threshold value α by administering the contrast agent. The vessel running data generating unit 31 thereby detects the vascular region of the coronary artery. The vessel running data generating unit 31 sets the reference point (the first reference point) inside the detected vascular region, and generates the centerline data with the reference point as the origin (step S4 in FIG. 12).

The lesion site detecting unit 32 of the vessel shape analyzing unit 3 then detects the positional information of the stenosis site in the coronary artery based on the vascular region data and the centerline data of the coronary artery supplied from the vessel running data generating unit 31 (step S5 in FIG. 12). The lesion degree measuring unit 33 measures the stenosis rate of the stenosis site by comparing the cross sectional area of the coronary artery in the stenosis site detected by the lesion site detecting unit 32 with the cross sectional area of the normal coronary artery (step S6 in FIG. 12).

The coronary artery dominant region data generating unit 41 of the dominant region data generating unit 4 receives the instruction signal for starting the generation of the diagnostic image data from the system control unit 10. The coronary artery dominant region data generating unit 41 thereby binarizes the volume data of the predetermined heartbeat time phase read out from the volume data storing unit 1, and generates the three-dimensional myocardial region data. Subsequently, the coronary artery dominant region data generating unit 41 sets the plurality of reference points (the third reference points) at the predetermined interval on the three-dimensional centerline data supplied from the vessel running data generating unit 31 of the vessel shape analyzing unit 3. The coronary artery dominant region data generating unit 41 forms the segment dominant regions dominated by the respective reference points in the myocardial region data based on the centerline data in which the reference points are set, and the myocardial region data. The obtained plurality of segment dominant regions are synthesized, to generate the coronary artery dominant region data (step S7 in FIG. 12).

The lesion site dominant region data generating unit 42 of the dominant region data generating unit 4 subsequently receives the positional information of one or a plurality of stenosis sites supplied from the lesion site detecting unit 32 of the vessel shape analyzing unit 3, and extracts the reference point corresponding to each of the stenosis sites from the plurality of reference points set on the centerline data. The lesion site dominant region data generating unit 42 further extracts all the reference points set on the downstream side of the reference point corresponding to the stenosis site from the plurality of reference points, and synthesizes the plurality of segment dominant regions formed by the coronary artery dominant region data generating unit 41 with respect to the obtained respective reference points. The lesion site dominant region data generating unit 42 thereby generates the three-dimensional lesion site dominant region data (step S8 in FIG. 12).

The functional image data generating unit 51 of the ischemic region data generating unit 5 receives the instruction signal for starting the generation of the diagnostic image data from the system control unit 10. The functional image data generating unit 51 thereby extracts the plurality of volume data of the predetermined heartbeat time phase based on the time point when the contrast agent is administered from the time-series volume data preliminarily stored in the volume data storing unit 1. The functional image data generating unit 51 processes the volume data to generate the myocardial perfusion image data (step S9 in FIG. 12).

The ischemic region extracting unit 52 of the ischemic region data generating unit 5 subsequently compares the voxel values of the myocardial perfusion image data generated by the functional image data generating unit 51 with the threshold value γ set in the step S2, and extracts the region with a smaller voxel value than the threshold value γ as the ischemic region. The ischemic region extracting unit 52 thereby generates the three-dimensional ischemic region data (step S10 in FIG. 12).

The overlapping rate computing unit 61 of the involvement rate computing unit 6 computes the overlapping rate of the three-dimensional lesion site dominant region data supplied from the lesion site dominant region data generating unit 42 of the dominant region data generating unit 4 and the three-dimensional ischemic region data supplied from the ischemic region extracting unit 52 of the ischemic region data generating unit 5 (step S11 in FIG. 12). The arithmetic unit 62 of the involvement rate computing unit 6 multiplies the overlapping rate of the lesion site dominant region data and the ischemic region data supplied with respect to each stenosis site from the overlapping rate computing unit 61, by the stenosis rate supplied with respect to each stenosis site from the lesion degree measuring unit 33 of the vessel shape analyzing unit 3. The arithmetic unit 62 thereby computes the ischemia involvement rate of the stenosis site (step S12 in FIG. 12).

The diagnostic image data generating unit 7 receives the three-dimensional coronary artery dominant region data and lesion site dominant region data generated in the dominant region data generating unit 4, and the three-dimensional ischemic region data generated in the ischemic region data generating unit 5. The diagnostic image data generating unit 7 subsequently superimposes the above various region data on the three-dimensional image data supplied from the morphological image data generating unit 2, and further adds thereto the computational result of the ischemia involvement rate supplied with respect to each stenosis site from the involvement rate computing unit 6. The diagnostic image data is thereby generated. The obtained diagnostic image data is displayed on the display unit 8 (step S13 in FIG. 12).

When the operator inputs an instruction signal to display the MPR image data of a stenosis site shown in the diagnostic image data, and a signal to select the stenosis site in the input unit 9 while observing the diagnostic image data displayed on the display unit 8, the MPR image data generating unit 22 of the morphological image data generating unit 2 receives the signals via the system control unit 10. The MPR image data generating unit 22 thereby forms the planar or curved MPR section (the first MPR section) including the centerline data within a predetermined range around the stenosis site, and the MPR section (the second MPR section) including the stenosis site and perpendicular to the centerline data based on the centerline data of the coronary artery supplied from the vessel running data generating unit 31 of the vessel shape analyzing unit 3 and the positional information of the stenosis site supplied from the lesion site detecting unit 32.

The first MPR section and the second MPR section are then set with respect to the volume data of the predetermined heartbeat time phase read out from the volume data storing unit 1, and the voxels of the volume data existing on the MPR sections are extracted. The MPR image data around the stenosis site is thereby generated.

The diagnostic image data generating unit 7 generates new diagnostic image data by adding the MPR image data supplied from the MPR image data generating unit 22 to the diagnostic image data generated in the step S13. The obtained diagnostic image data is displayed on the display unit 8.

Next, clinical importance of the ischemia involvement rate shown in the diagnostic image data of the present embodiment will be described based on FIG. 13. FIG. 13 shows a specific example of the stenosis rates and the overlapping rates used for computing the ischemia involvement rates in the stenosis sites Rs1 to Rs4. For example, the stenosis sites Rs1 and Rs3 have a relatively high stenosis rate, but the lesion site dominant region and the ischemic region do not overlap therein. Thus, the ischemia involvement rate thereof is 0%. It is therefore diagnosed that treatment for the stenosis sites has a low priority. Meanwhile, the stenosis site Rs2 has a relatively low stenosis rate, but the lesion site dominant region and the ischemic region largely overlap therein. Thus, the ischemia involvement rate thereof is relatively high, i.e., 25%. It is therefore diagnosed that the stenosis site Rs2 needs to be immediately treated. By displaying the ischemia involvement rate in the vicinity of the stenosis site shown in the various image data and the various region data, a preferable course of treatment for the stenosis site can be easily determined.

According to the embodiment of the present disclosure described above, the three-dimensional image data is generated on the cardiac region of an object having coronary arterial disease based on the volume data collected from the object by the medical image diagnosis apparatus. The three-dimensional image data is displayed with the lesion site dominant region data or the ischemic region data generated based on the volume data being superimposed thereon. Ischemic heart disease can be thereby accurately and easily diagnosed.

The ischemia involvement rate is obtained based on the overlapping rate of the ischemic region in the ischemic region data and the lesion site dominant region in the lesion site dominant region data, and the stenosis rate of the stenosis site measured based on the volume data. The ischemia involvement rate is added to the three-dimensional image data or the various region data. Whether the stenosis site is involved in the ischemic region, and the degree of involvement rate can be thereby quantitatively and objectively understood. Accordingly, a preferable course of treatment for the stenosis site can be determined in short time.

According to the above embodiment, the MPR image data of the coronary artery or the myocardial tissue around the stenosis site can be displayed based on the selection signal of the stenosis site input by an operator or the like. Therefore, a condition of a stenosis site having a high ischemia involvement rate can be observed in detail, for example.

Although the embodiment of the present disclosure has been described above, the present disclosure is not limited to the aforementioned embodiment, and may be embodied in a modified manner. For example, the aforementioned embodiment employs the case in which the diagnostic image data is generated in order to diagnose the ischemic heart disease by use of the volume data supplied from the separately-installed medical image diagnosis apparatus such as an X-ray CT apparatus and an MRI apparatus via a network or a storage medium. However, the volume data may be supplied directly from the medical image diagnosis apparatus. The medical image processing apparatus 100 may be also a portion of the medical image diagnosis apparatus.

The aforementioned embodiment employs the case in which the myocardial perfusion image data is generated as the functional image data by accumulating the preliminarily-collected time-series volume data, and the three-dimensional image data is generated as the morphological image data by rendering the volume data of the predetermined heartbeat time phase extracted from the time-series volume data. However, another image data may be generated as the functional image data or the morphological image data.

In the aforementioned embodiment, the vessel running data generating unit 31 generates the centerline data as the vessel running data by a tracking method using the search vector. However, the present disclosure is not limited thereto. For example, the vascular region of the coronary artery extracted by binarizing the volume data may be subjected to a thinning process, to thereby generate the vessel running data.

In the aforementioned embodiment, the lesion site detecting unit 32 detects the stenosis site by comparing the cross sectional area of the coronary artery measured at each of the reference points Pm with the predetermined threshold value β. However, the stenosis site may be detected based on a maximum vessel diameter or an average vessel diameter at the reference points Pm.

In the aforementioned embodiment, the coronary artery dominant region data generating unit 41 performs the dilation process on the voxels included in the myocardial region from the reference voxels Gf (f=1 to F) on the myocardial tissue surface at a constant speed (see FIGS. 6A to 6D). However, for example, the dilation process may be performed at a speed corresponding to the cross sectional area of the coronary artery or the above vessel diameter measured at each of the reference points Pm by the lesion site detecting unit 32. By applying such dilation process, the dominant region data can be more accurately generated.

In the aforementioned embodiment, the diagnostic image data is displayed in a display manner as shown in FIG. 13. However, the display manner is not limited thereto. For example, the diagnostic image data may be displayed as a Polar-Map image having a polar coordinate system as shown in FIG. 14. In this case, the morphological image data (the three-dimensional image data), the ischemic region data, the coronary artery dominant region data, and the lesion site dominant region data constituting the diagnostic image data are also generated using similar polar coordinate systems.

In the aforementioned embodiment, the ischemic region extracting unit 52 of the ischemic region data generating unit 5 extracts the ischemic region of the myocardial perfusion image data by comparing the voxel values of the myocardial perfusion image data generated by the functional image data generating unit 51 with the threshold value γ set in the initial setting in the step S2. However, the threshold value γ may be renewed during the generation of the diagnostic image data. That is, the operator of the medical image processing apparatus 100 renews the threshold value γ in the input unit 9 while observing the diagnostic image data displayed on the display unit 8. The diagnostic image data generating unit 7 generates new diagnostic image data based on ischemic region data generated by the ischemic region data generating unit 5 based on the renewed threshold value γ, and the morphological image data, the coronary artery dominant region data and the lesion site dominant region data which have been already obtained. The new diagnostic image data is displayed on the display unit 8. In this case, the new diagnostic image data is generated by adding an ischemia involvement rate computed by the involvement rate computing unit 6 based on the ischemic region data obtained by the renewed threshold value γ to the above image data or the region data.

In the aforementioned embodiment, the MPR image data of the stenosis site selected in the input unit 9 while the diagnostic image data is being observed is generated/displayed. However, the MPR image data may be automatically generated/displayed on a stenosis site having a highest ischemia involvement rate. Alternatively, the MPR image data may be generated on each of the stenosis sites and sequentially displayed in descending order of ischemia involvement rate, for example. In this case, the stenosis site, the centerline data, the computational result of the ischemia involvement rate or the like corresponding to the MPR image data being displayed are emphasized (highlighted) on different display conditions (for example, in a different color tone) in the diagnostic image data.

In the present embodiment, the segment dominant regions constituting the coronary artery dominant region data are formed by the dilation process from the reference points Paf arranged at the predetermined interval Δe on the centerline data. However, the segment dominant regions may be also formed by another method. For example, the segment dominant regions may be formed or the coronary artery dominant region data may be generated by applying a global standard classification method of dividing a myocardial region into 17 segments and defining a coronary artery that dominates each of the segments, which is advocated by the AHA (American Heart Association). In this case, a segment number is added to the coronary artery dominant region data, so that the stenosis site can be more easily detected.

The medical image processing apparatus 100 according to the present embodiment may be partly achieved by using a computer as hardware, for example. For example, various functions of the system control unit 10 or the like may be achieved by causing a processor such as a CPU mounted in the computer to execute a predetermined control program. In this case, the system control unit 10 may be achieved by installing the control program on the computer in advance, or installing on the computer a control program stored in a storage medium readable by the computer or distributed via a network.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:
1. A medical image processing apparatus comprising:
a vessel running data generator configured to generate vessel running data of a vessel based on volume data collected by a medical image diagnosis apparatus;
a lesion site detector configured to detect positional information of a lesion site in the vessel based on the volume data;
a vessel dominant region data generator configured to generate vessel dominant region data indicating a region dominated by the vessel in a region provided with nutrition based on the vessel running data;
a lesion site dominant region data generator configured to generate lesion site dominant region data indicating a region dominated by the lesion site in the region provided with nutrition based on the vessel running data and the positional information of the lesion site;
an ischemic region data generator configured to generate ischemic region data indicating an ischemic region in the region provided with nutrition based on the functional image data; and
a diagnostic image data generator configured to generate diagnostic image data by superimposing the vessel dominant region data, the lesion site dominant region data and the ischemic region data on morphological image data or functional image data generated based on the volume data.

2. The medical image processing apparatus according to claim 1, wherein
the vessel is a coronary artery, and the region provided with nutrition is a myocardial region.

3. The medical image processing apparatus according to claim 1, wherein
the vessel dominant region data generator generates the vessel dominant region data by performing a dilation process on the region provided with nutrition from reference points set at a predetermined interval on the vessel running data.

4. The medical image processing apparatus according to claim 3, wherein
wherein the vessel dominant region data generator generates the vessel dominant region data by forming a plurality of segment dominant regions in the region provided with nutrition by the dilation process from each of the reference points and synthesizing the plurality of segment dominant regions.

5. The medical image processing apparatus according to claim 4, wherein
the lesion site dominant region data generator extracts a reference point corresponding to the lesion site and a plurality of reference points existing on a downstream side of the reference point from the plurality of reference points set on the vessel running data, and generates the lesion site dominant region data based on segment dominant regions formed with respect to the reference points by the vessel dominant region data generator.

6. The medical image processing apparatus according to claim 1, further comprising:
a morphological image data generator configured to generate the morphological image data, wherein
the morphological image data generator generates at least one of three-dimensional image data and MPR (Multi Planner Reconstruction) image data including the lesion site as the morphological image data based on the volume data.

7. The medical image processing apparatus according to claim 1, further comprising:
a functional image data generator configured to generate the functional image data, wherein
the functional image data generator generates perfusion image data as the functional image data based on the volume data.

8. The medical image processing apparatus according to claim 1, wherein
the ischemic region data generator generates the ischemic region data by comparing a voxel value or a pixel value of perfusion image data generated based on the volume data with a predetermined threshold value and thereby extracting the ischemic region in the perfusion image data.

9. The medical image processing apparatus according to claim 1, wherein
the diagnostic image data generator generates three-dimensional diagnostic image data based on the morphological image data or the functional image data, the vessel dominant region data, the lesion site dominant region data and the ischemic region data which are generated in three dimensions based on the volume data.

10. The medical image processing apparatus according to claim 1, further comprising:
a lesion degree detector configured to measure a lesion degree of the lesion site, wherein
the diagnostic image data generator generates the diagnostic image data by adding the measured lesion degree to the morphological image data or the functional image data on which the vessel dominant region data, the lesion site dominant region data and the ischemic region data are superimposed.

11. The medical image processing apparatus according to claim 10, further comprising:
a calculator configured to compute an overlapping rate of the lesion site dominant region in the lesion site dominant region data and the ischemic region in the ischemic region data, wherein
the diagnostic image data generator generates the diagnostic image data by adding the measured lesion degree and the computed overlapping rate to the morphological image data or the functional image data on which the vessel dominant region data, the lesion site dominant region data and the ischemic region data are superimposed.

12. The medical image processing apparatus according to claim 11, further comprising:
an involvement rate calculator configured to compute an ischemia involvement rate based on the lesion degree, the ischemic region data, and the lesion site dominant region data, wherein
the diagnostic image data generator generates the diagnostic image data by adding the measured lesion degree, the computed overlapping rate and the computed ischemia involvement rate to the morphological image data or the functional image data on which the vessel dominant region data, the lesion site dominant region data and the ischemic region data are superimposed.

13. The medical image processing apparatus according to claim 12, wherein
the involvement rate calculator computes the overlapping rate of the lesion site dominant region in the lesion site dominant region data and the ischemic region in the ischemic region data, and computes the ischemia involvement rate based on the overlapping rate and the lesion degree such as a stenosis rate of the lesion site measured by the lesion degree detector.

14. The medical image processing apparatus according to claim 12, further comprising:
a display controller configured to display the diagnostic image data on a display device, wherein
the display controller emphasizes the lesion site or the lesion site dominant region according to the computed ischemia involvement rate.

15. The medical image processing apparatus according to claim 12, further comprising:
a display controller configured to display the diagnostic image data on a display device, wherein
the display controller control unit displays the diagnostic image data as a Polar-Map image having a polar coordinate system.

16. The medical image processing apparatus according to claim 6, further comprising:
a stenosis site selector configured to select a stenosis site as the lesion site, wherein
the diagnostic image data generator generates the diagnostic image data by using MPR image data generated by the morphological image data generator with respect to the stenosis site selected by the stenosis site selector.

17. A medical image processing method comprising:
obtaining volume data collected by a medical image diagnosis apparatus from a storing unit;
generating vessel running data of a vessel based on the obtained volume data;

detecting positional information of a lesion site in the vessel based on the volume data;

generating vessel dominant region data indicating a region dominated by the vessel in a region provided with nutrition based on the vessel running data;

generating lesion site dominant region data indicating a region dominated by the lesion site in the region provided with nutrition based on the vessel running data and the positional information of the lesion site;

generating diagnostic image data by superimposing the vessel dominant region data and the lesion site dominant region data on morphological image data or functional image data generated based on the volume data;

generating ischemic region data indicating an ischemic region in the region provided with nutrition based on the functional image data, wherein the diagnostic image data generating generates the diagnostic image data by superimposing the vessel dominant region data, the lesion site dominant region data and the ischemic region data on the morphological image data or the functional image data; and displaying the diagnostic image data on the display unit.

18. The medical image processing method according to claim 17, further comprising:

measuring a lesion degree of the lesion site, wherein the diagnostic image data generating generates the diagnostic image data by adding the measured lesion degree to the morphological image data or the functional image data on which the vessel dominant region data, the lesion site dominant region data and the ischemic region data are superimposed.

19. The medical image processing method according to claim 18, further comprising:

computing an overlapping rate of the lesion site dominant region in the lesion site dominant region data and the ischemic region in the ischemic region data, wherein the diagnostic image data generating generates the diagnostic image data by adding the measured lesion degree and the computed overlapping rate to the morphological image data or the functional image data on which the vessel dominant region data, the lesion site dominant region data and the ischemic region data are superimposed.

20. The medical image processing method according to claim 19, further comprising:

computing an ischemia involvement rate based on the lesion degree, the ischemic region data, and the lesion site dominant region data, wherein the diagnostic image data generating generates the diagnostic image data by adding the measured lesion degree, the computed overlapping rate and the computed ischemia involvement rate to the morphological image data or the functional image data on which the vessel dominant region data, the lesion site dominant region data and the ischemic region data are superimposed.

* * * * *